United States Patent
Wang et al.

(10) Patent No.: US 11,614,444 B2
(45) Date of Patent: Mar. 28, 2023

(54) TIME-RESOLVED FLUORESCENCE IMMUNOCHROMATOGRAPHY TEST PAPER CARD FOR DETECTING BUTRALIN

(71) Applicant: Tobacco Research Institute of Chinese Academy of Agricultural Sciences, Qingdao (CN)

(72) Inventors: Xiuguo Wang, Qingdao (CN); Xiao Zheng, Qingdao (CN); Yalei Liu, Qingdao (CN); Kuan Fang, Qingdao (CN); Xiaolian Zhang, Qingdao (CN)

(73) Assignee: TOBACCO RESEARCH INSTITUTE OF CHINESE ACADEMY OF AGRICULTURAL SCIENCES, Qingdao (CN)

(*) Notice: Subject to any disclaimer, the term of this patent is extended or adjusted under 35 U.S.C. 154(b) by 291 days.

(21) Appl. No.: 16/939,558

(22) Filed: Jul. 27, 2020

(65) Prior Publication Data
US 2021/0215678 A1 Jul. 15, 2021

(51) Int. Cl.
*G01N 33/53* (2006.01)
(52) U.S. Cl.
CPC .............................. *G01N 33/5302* (2013.01)
(58) Field of Classification Search
CPC ........... G01N 33/54386; G01N 33/558; G01N 33/54387; G01N 33/54388; G01N 33/54389; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS

| | | | | |
|---|---|---|---|---|
| 5,160,701 A | * | 11/1992 | Brown, III | G01N 33/54366 436/535 |
| 5,212,065 A | * | 5/1993 | Pegg | G01N 33/54366 436/805 |
| 5,658,801 A | * | 8/1997 | Poissant | B01L 3/5023 436/514 |
| 7,569,397 B2 | * | 8/2009 | Esfandiari | G01N 33/558 436/805 |

FOREIGN PATENT DOCUMENTS

| | | | | |
|---|---|---|---|---|
| CN | 106771159 A | * | 5/2017 | .......... G01N 33/558 |
| CN | 109061145 A | | 12/2018 | |

(Continued)

*Primary Examiner* — Bao-Thuy L Nguyen
*Assistant Examiner* — Estifanos Hailu
(74) *Attorney, Agent, or Firm* — Nolte Lackenbach Siegel

(57) ABSTRACT

A time-resolved fluorescence immunochromatography test paper card for detecting butralin, which comprises a cover body and a housing body, wherein the cover body is provided with a test hole, a loading hole and a through-hole, an isolating mechanism is arranged in the test hole and the loading hole, the isolating mechanism comprises a first isolating ring and a second isolating ring, the top lateral walls of which are respectively provided with a first lug boss and a second lug boss, one end of the upper surface of the working board is concave towards the inner of the working board to provide a groove, there is a nitrocellulose membrane, a binding pad, a sample pad and a mark zone successively provided between the water absorbing block and the other end of the working board, and the lateral wall at one end of the working board is provided with a bump.

7 Claims, 2 Drawing Sheets

(56) References Cited

FOREIGN PATENT DOCUMENTS

| CN | 109061147 A | | 12/2018 | |
|---|---|---|---|---|
| CN | 109061148 A | | 12/2018 | |
| CN | 109061149 A | * | 12/2018 | ......... G01N 21/6408 |
| CN | 109061149 A | | 12/2018 | |
| CN | 109061156 A | | 12/2018 | |
| CN | 109061157 A | | 12/2018 | |
| CN | 109324182 A | | 2/2019 | |
| WO | WO-2017087831 A1 | * | 5/2017 | ........... G01N 33/558 |
| WO | WO-2017117022 A1 | * | 7/2017 | ....... G01N 33/54386 |

* cited by examiner

TIME-RESOLVED FLUORESCENCE IMMUNOCHROMATOGRAPHY TEST PAPER CARD FOR DETECTING BUTRALIN

CROSS-REFERENCE TO RELATED APPLICATIONS

This Application claims priority to, and the benefit of, China Patent Application No. 202010028344.9, filed Jan. 10, 2020.

TECHNICAL FIELD

The disclosure pertains to the technical field of detection, and specifically pertains to a time-resolved fluorescence immunochromatography test paper card and associated apparatus for detecting butralin.

BACKGROUND

Butralin, also known as germ inhibitor, with a chemical name of N-sec-butyl-4-tert-butyl-2,6-dinitroaniline, is a dinitroaniline herbicide and a plant growth regulator developed by American Amchem Co. at the late 1960s. Its original medicine is an orange crystal and soluble in organic solvents. As a selective herbicide, it can inhibit the cell division and differentiation through the absorption of plant buds, caulicles and roots, and then inhibit the growth of radicles and buds, finally leading to the lodging, distortion and growth stagnation and death of plants. Butralin can also be used as a plant growth regulator to inhibit the growth of tobacco axillary buds. It has attracted more and more attention due to its good control effect, wide application range, large consumption, and low pesticide residue.

All countries in the world have prescribed the limit of butralin in food, and carried out daily monitoring of butralin in samples for random checking in the market. At present, processes for detecting butralin residue mainly include chromatography, colloidal gold immunochromatography, etc. Chromatography generally requires large instruments, such as gas chromatograph, gas chromatograph-mass spectrometer, and the like, and is tedious, time-consuming and requires high professional requirements for operators, thus being not suitable for quick detection on site. Enzyme-linked immunosorbent assay ("ELISA") and colloidal gold immunochromatography each feature simple operation, rapid detection, but poor accuracy and repeatability, so it is impossible to achieve quantitative detection, and matrix effect has a great influence, so it is easy to cause false positive or false negative results. Immunochromatographic detection technology is a detection technology developed on the basis of the immunolabelling technique and chromatography which is used for detecting antigens, antibodies or haptens. This detection technology is characterized by the application of antigen-antibody specific immunological response and chromatography, and in the form of a test paper, to achieve rapid, accurate and specific color-developing to detect the object, which, compared to ELISA and colloidal gold immunochromatography, is universal, fast, easy to operate, has quick and stable results, and is becoming an increasing common method in the field of food detection.

The time-resolved fluorescence immunochromatography test paper card is an important detection tool in the immunochromatographic detection technology. The existing time-resolved fluorescence immunochromatography test paper cards are easy to be confused due to large testing quantity during the processes of field detection at the base level and large-throughput rapid screening detection, and most of them are disposable appliances, with high cost.

Therefore, it is urgent to develop a time-resolved fluorescence immunochromatography test paper card for detecting butralin, with simple operation, high accuracy, and low cost.

SUMMARY

To overcome the deficiencies in the prior art, the present invention aims to provide a time-resolved fluorescence immunochromatography test paper card and an associated apparatus for detecting butralin.

The present invention provides the following technical scheme:

A time-resolved fluorescence immunochromatography test paper card for detecting butralin, the test paper card (also referred to herein as a working board) may be inserted into an apparatus comprising a cover body and a housing body, wherein the cover body is provided with a test hole, a loading hole, and a through-hole, an isolating mechanism is arranged in the test hole and the loading hole, the isolating mechanism comprises a first isolating ring and a second isolating ring, the top lateral walls of each isolating ring are respectively provided with a first lug boss and a second lug boss, one end of the first lug boss is connected to one end of the second lug boss through a connecting sheet, the inner wall of the second lug boss is provided with a filter screen, the interior of the housing body is provided with a first clamping groove and a second clamping groove arranged oppositely with respect to each other to hold a working board. In use, respective ends of the working board are connected to the first clamping groove and the second clamping groove, a damper is provided at the edge of the upper surface of the working board, one end of the upper surface of the working board is concave towards the inner of the working board to provide a groove, the interior of the groove is provided with a water absorbing block, there is a nitrocellulose membrane, a binding pad, a sample pad, and a mark zone successively provided sequentially between the water absorbing block and the other end (end opposite groove) of the working board, and the lateral wall at one edge of the working board is provided with a bump.

Preferably, one side or edge of the cover body is hinged with one side or edge of the housing body through a hinge to allow opening and closing of the cover body with respect to the housing body.

Preferably, the first isolating ring and the second isolating ring are inserted into the test hole and the loading hole respectively, and a lower surface of the first lug boss, the connecting sheet and the second lug boss are all in contact with an upper surface of the cover body.

Preferably, one end of the sample pad is overlapped on an upper surface at a first end of the binding pad, the second end of the binding pad is overlapped on a first end of the nitrocellulose membrane, a side wall at the second end of the nitrocellulose membrane is connected to a side wall at a first end of the water absorbing block, an acute angle is formed between a plane on which the side wall at a first end of the groove is located and the upper surface of the working board, the bottom at the second end of the nitrocellulose membrane is clamped with the side wall at a first end of the groove.

Preferably, the sample pad, the binding pad, the nitrocellulose membrane, and the water absorbing block all have the same width. T, the binding pad comprises a detecting microsphere and a quality control microsphere, the detecting microsphere is a fluorescent microsphere coated with butralin monoclonal antibody, the quality control microsphere is a fluorescent microsphere coated with rabbit anti-marker protein, the nitrocellulose membrane is provided with a detection line and a quality control line, the lengths of the detection line and the quality control line are both the same as the width of the nitrocellulose membrane, the detection line is coated with butralin antigen, and the quality control line is coated with anti-rabbit antibody.

Preferably, one end of the bump is connected to the lateral wall at one end of the working board, the other end of the bump is provided with a magnet, the side wall at the other end of the working board is made of iron. When not in use, the magnet of one working board and the iron side of the other working board are attracted together, thereby connecting multiple working boards together in parallel for being easy to store and arrange.

Preferably, the location of the mark zone corresponds to that of the through-hole.

The present invention has the following beneficial effects: Opening a quantitative analyzer (not shown), obtaining a working board and a housing body connected to each other; after the mark zone is marked, a working board is taken out and installed between the first clamping groove and the second clamping groove of the housing body; closing the cover body, the location of the loading hole corresponds to that of the sample pad, the location of the test hole corresponds to those of the quality control line and the detection line, and the location of the through-hole corresponds to that of the mark zone, with high accuracy to avoid sample confusion. The isolating mechanism is arranged on the test hole and the loading hole. When loading, samples are added via the inner wall of the second isolating ring, the solid impurities in samples would stay over the filter screen, so that the sample content absorbed by each sample pad is kept relatively consistent. The edge of the test hole is enclosed by the first lug boss and the first isolating ring, and the edge of the loading hole is enclosed by the second lug boss and the second isolating ring, to prevent the sample of butralin from contacting the cover body and affecting the test result of the next sample. After loading, the whole apparatus with the samples are placed into a quantitative analyzer to detect and the results are recorded. After detection, the operator takes out the apparatus from the quantitative analyzer, opens the cover body, and takes out the working board from the first clamping groove and the second clamping groove through holding a bump. Then, the operator disassembles the isolating mechanism from the cover body, takes out a row of unused working board, separates the magnet from the side wall of its adjacent working board, takes out a marked working board again and arranges it between the first clamping groove and the second clamping groove of the housing body, closes the cover body and arranges a new isolating mechanism in the test hole and the loading hole, the above operations may then be repeated. The present invention is simple in operation and can reduce the cost during large-throughput rapid screening detection.

BRIEF DESCRIPTION OF THE DRAWINGS

The appended drawings are provided for further understanding the invention, and constitute a part of the specification, which are used to interpret the invention together with embodiments of the invention, but not constitute a limitation to the invention. In the appended drawings.

The figures are marked as: 1. cover body; 2. housing body; 3. test hole; 4. loading hole; 5. through-hole; 6. the first isolating ring; 7. the second isolating ring; 8. the first lug boss; 9. the second lug boss; 10. connecting sheet; 11. the first clamping groove; 12. the second clamping groove; 13. damper; 14. water absorbing block; 15. nitrocellulose membrane; 16. binding pad; 17. sample pad; 18. mark zone; 19. bump; 20. hinge; 21. detection line; 22. quality control line; 23. magnet; 24. working board; 25. filter screen; 26. groove; 27 iron side; 28 first end of nitrocellulose membrane; 29 second end of nitrocellulose membrane; 30 first end of binding pad; 31 second end of binding pad; 32 first end of water absorbing block; 33 first end of groove; 34 upper surface of working board.

DESCRIPTION OF THE EMBODIMENTS

Figure 1:
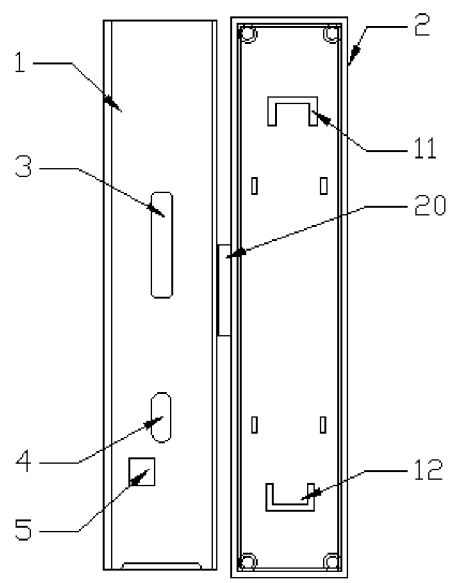
FIG. 1 is a schematic diagram of the internal structure of the housing body and the cover body in the invention.
Figure 2:
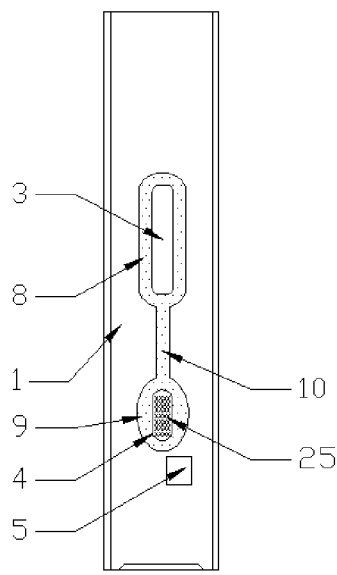
FIG. 2 is a top view of the cover body in the invention.
Figure 3:
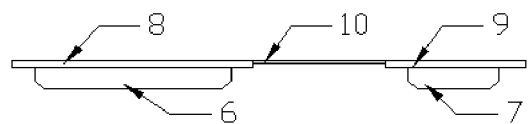
FIG. 3 is a left view of the isolating mechanism in the invention.
Figure 4:
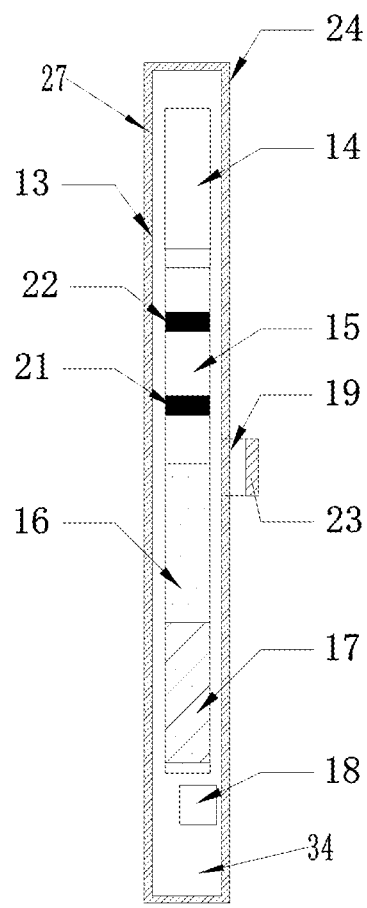
FIG. 4 is a front view of the working board in the invention.
Figure 5:
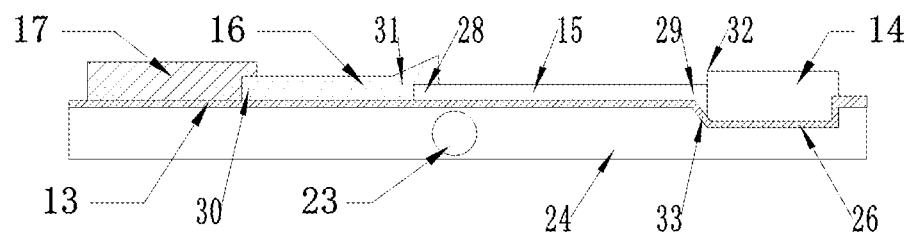
FIG. 5 is a right view of the working board in the invention.

As shown in FIGS. 1 to 5, a time-resolved fluorescence immunochromatography test paper card for detecting butralin, comprising a cover body 1 and a housing body 2, wherein the cover body 1 is provided with a test hole 3, a loading hole 4 and a through-hole 5, an isolating mechanism is arranged in the test hole 3 and the loading hole 4, the isolating mechanism comprises a first isolating ring 6 and a second isolating ring 7, the top lateral walls of which are respectively provided with a first lug boss 8 and a second lug boss 9, one end of the first lug boss 8 is connected to one end of the second lug boss 9 through a connecting sheet 10, the inner wall of the second lug boss 9 is provided with a filter screen 25, the interior of the housing body 2 is provided with a first clamping groove 11 and a second clamping groove 12 arranged oppositely, two ends of a working board 24 are connected to the first clamping groove 11 and the second clamping groove 12 respectively, a damper 13 is provided at the edge of the upper surface of the working board 34, one end of the upper surface of the working board 34 is concave towards the inner of the working board 24 to provide a groove 26, the interior of the groove 26 is provided with a water absorbing block 14, there is a nitrocellulose membrane 15, a binding pad 16, a sample pad 17 and a mark zone 18 successively provided between the water absorbing block 14 and the other end of the working board 24, and the lateral wall at one end of the working board is provided with a bump 19.

One end of the cover body 1 is hinged with one end of the housing body 2 through a hinge 20. The first isolating ring 6 and the second isolating ring 7 are inserted into the test hole 3 and the loading hole 4 respectively, and the first lug boss 8, the connecting sheet 10 and a lower surface of the second lug boss 9 are all connected to an upper surface of the cover body 1. One end of the sample pad 17 is overlapped on an upper surface at a first end of the binding pad 30, the second end of the binding pad 31 is overlapped on a first end of the nitrocellulose membrane 29, a side wall at the second end of the nitrocellulose membrane 29 is connected to a side wall at a first end of the water absorbing block 32, an acute angle is formed between a plane on which the side wall at a first end of the groove 33 is located and the upper surface of the working board 34, the bottom at the second end of the nitrocellulose membrane 29 is clamped with the side wall at a first end of the groove 33. The sample pad 17, the binding pad 16, the nitrocellulose membrane 15 and the water absorbing block 14 all have the same width. The binding pad 16 comprises a detecting microsphere and a quality control microsphere, the detecting microsphere is a fluorescent microsphere coated with butralin monoclonal antibody, the quality control microsphere is a fluorescent microsphere coated with rabbit anti-marker protein. The nitrocellulose membrane 15 is provided with a detection line 21 and a quality control line 22, the lengths of the detection line 21 and the quality control line 22 are both the same as the width of the nitrocellulose membrane 15, the detection line 21 is coated with butralin antigen, and the quality control line 22 is coated with anti-rabbit antibody. One end of the bump 19 is connected to the lateral wall at one end of the working board 24, the other end of the bump 19 is provided with a magnet 23. The side wall at the other end of the working board 24 is made of iron. The working board 24 is narrow and connected into a piece under the action of the magnet 23 for easy to take, and it is easier to separate from each other. When not in use, the magnet of one working board and the iron side 27 of the other working board are attracted together, thereby connecting multiple working boards together in parallel for being easy to store and arrange. The location of the mark zone 18 corresponds to that of the through-hole 5.

Embodiment

Opening a quantitative analyzer, obtaining a working board 24 and a housing body 2 connected to each other which correspond to the number of samples containing butralin; after the mark zone 18 is marked, a working board 24 is taken out and installed between the first clamping groove 11 and the second clamping groove 12 of the housing body 2; closing the cover body 1, the location of the loading hole 4 corresponds to that of the sample pad 17, the location of the test hole 3 corresponds to those of the quality control line 22 and the detection line 21, and the location of the through-hole 5 corresponds to that of the mark zone 18. The isolating mechanism is arranged on the test hole 3 and the loading hole 4. When loading, samples are added via the inner wall of the second isolating ring 7, the solid impurities in samples would stay over the filter screen 25. The edge of the test hole 3 is enclosed by the first lug boss 8 and the first isolating ring 6, and the edge of the loading hole 4 is enclosed by the second lug boss 9 and the second isolating ring 7, to prevent the sample of butralin from contacting the cover body 1 and affecting the test result of the next sample. After loading, the whole apparatus with the samples are placed into a quantitative analyzer to detect and the results are recorded. After detection, the operator takes out the apparatus from the quantitative analyzer, opens the cover body 1, and takes out the working board 24 from the first clamping groove 11 and the second clamping groove 12 through holding the bump 19. Then the operator disassembles the isolating mechanism from the cover body 1; takes out a row of unused working board 24, separates the magnet 23 from the side wall of its adjacent working board 24, takes out a marked working board 24 again and arranges it between the first clamping groove 11 and the second clamping groove 12 of the housing body 2, closes the cover body 1 and arranging a new isolating mechanism in the test hole 3 and the loading hole 4, the above operations may then be repeated.

The foregoing is only a preferred embodiment of the invention and is not used to limit the invention. Notwithstanding the present invention has been described in detail with reference to the foregoing embodiment, the skilled persons may still modify the technical scheme recorded in the aforementioned embodiment, or replace some of the technical features equivalently. Any modifications, equivalent replacements or improvements within the spirit and principle of the invention should all be included in the scope of protection of the invention.

What is claimed is:

1. An apparatus using test paper card for detecting butralin, comprising:
   a cover body; and
   a housing body;
   wherein the cover body provided with a test hole, a loading hole, a through-hole, an isolating mechanism arranged in the test hole and the loading hole, the isolating mechanism comprising a first isolating ring and a second isolating ring, a top outer peripheral wall of the first isolating ring and a top outer peripheral side of the second isolating ring respectively provided with a first lug boss and a second lug boss, one end of the first lug boss connected to one end of the second lug boss through a connecting sheet, an inner peripheral wall of the second lug boss provided with a filter screen, the housing body having a first clamping groove and a second clamping groove arranged opposite to each other disposed therein, two longitudinal ends of a working board connected to the first clamping groove and the second clamping groove respectively, a damper provided at an edge of an upper surface of the working board, the upper surface of the working board concave, near one end of the two longitudinal ends, towards an inner portion of the working board to provide an additional groove, the additional groove having a water absorbing block provided therein, the apparatus further including a nitrocellulose membrane, a binding pad, a sample pad and a mark zone sequentially provided between the water absorbing block and another longitudinal end of the working board, and the working board having a bump provided on its outside wall located at its lateral end.

2. The apparatus according to claim 1, wherein one end of the cover body is hinged with one end of the housing body through a hinge.

3. The apparatus according to claim 2, wherein the first isolating ring and the second isolating ring are inserted into the test hole and the loading hole respectively, and lower surfaces of the first lug boss, the connecting sheet, and the second lug boss are all in contact with the upper surface of the cover body.

4. The apparatus according to claim 3, wherein one end of the sample pad is overlapped on a portion of an upper surface of the binding pad located at one end of the binding pad, another end of the binding pad is overlapped with one end of the nitrocellulose membrane, an outside wall of the nitrocellulose membrane located at its another end opposite the one end, is connected to an outside wall of the water absorbing block at its one end, an acute angle is formed between a plane on which an inside wall of the additional groove at its one end adjacent to the one end of the water absorbing block is located and the upper surface of the working board, a bottom of the nitrocellulose membrane at its another end is clamped with the inside wall of the additional groove at its one end.

5. The apparatus according to claim 4, wherein the sample pad, the binding pad, the nitrocellulose membrane and the water absorbing block all have a same width, the binding pad comprises a detecting microsphere and a quality control microsphere, the detecting microsphere is a fluorescent microsphere coated with butralin monoclonal antibody, the quality control microsphere is a fluorescent microsphere coated with rabbit anti-marker protein, the nitrocellulose membrane is provided with a detection line and a quality control line, a length of the detection line and a length of the quality control line are both equal to a width of the nitrocellulose membrane, the detection line is coated with butralin antigen, and the quality control line is coated with anti-rabbit antibody.

6. The apparatus according to claim 5, wherein a first end of the bump is connected to an outer peripheral wall of the working board located at its lateral end, a second end of the bump is provided with a magnet, an outside wall of the working board located at the lateral end is made of iron.

7. The apparatus according to claim 6, wherein a location of the mark zone corresponds to a location of the through-hole.

* * * * *